(12) United States Patent
Tanida

(10) Patent No.: US 7,340,952 B2
(45) Date of Patent: Mar. 11, 2008

(54) CAPACITIVE HUMIDITY SENSOR

(75) Inventor: Katsunori Tanida, Kariya (JP)

(73) Assignee: Denso Corporation, Kariya (JP)

( * ) Notice: Subject to any disclaimer, the term of this patent is extended or adjusted under 35 U.S.C. 154(b) by 187 days.

(21) Appl. No.: 11/211,525

(22) Filed: Aug. 26, 2005

(65) Prior Publication Data
US 2006/0055503 A1 Mar. 16, 2006

(30) Foreign Application Priority Data
Sep. 14, 2004 (JP) ............................. 2004-267206

(51) Int. Cl.
*G01N 19/10* (2006.01)
(52) U.S. Cl. .................. 73/335.02; 73/29.05; 361/286
(58) Field of Classification Search ............. 73/334.02, 73/334.03, 334.04, 29.05; 361/286
See application file for complete search history.

(56) References Cited

U.S. PATENT DOCUMENTS

| | | | | |
|---|---|---|---|---|
| 4,057,823 A | * | 11/1977 | Burkhardt et al. | 257/414 |
| 4,598,333 A | * | 7/1986 | Adams et al. | 361/286 |
| 4,805,070 A | * | 2/1989 | Koontz et al. | 361/286 |
| 4,831,493 A | * | 5/1989 | Wilson et al. | 361/286 |
| 6,111,280 A | * | 8/2000 | Gardner et al. | 257/253 |
| 6,580,600 B2 | * | 6/2003 | Toyoda et al. | 361/523 |
| 6,647,782 B2 | * | 11/2003 | Toyoda | 73/335.04 |
| 6,690,569 B1 | * | 2/2004 | Mayer et al. | 361/303 |
| 7,092,232 B2 | * | 8/2006 | Yamagata et al. | 361/277 |
| 7,157,054 B2 | * | 1/2007 | Toyoda et al. | 422/88 |
| 2002/0114125 A1 | | 8/2002 | Toyoda et al. | |

FOREIGN PATENT DOCUMENTS

| JP | A-63-208751 | 8/1988 |
|---|---|---|
| JP | U-5-23124 | 3/1993 |

* cited by examiner

*Primary Examiner*—Michael Cygan
(74) *Attorney, Agent, or Firm*—Posz Law Group, PLC

(57) ABSTRACT

A capacitive humidity sensor includes a printed circuit board having an insulating substrate on which a circuit section is formed, a pair of electrodes formed on a surface of the insulating substrate to be opposite from each other with a space, and a humidity sensitive layer formed on the insulating substrate to cover the electrodes and the surface of the insulating substrate between the pair of electrodes. The relative permittivity of the humidity sensitive layer changes in response to humidity, and the circuit section performs a signal processing of a capacitance change between the electrodes. Furthermore, the electrodes and the circuit section are electrically connected through a wiring section formed in the insulating substrate.

7 Claims, 3 Drawing Sheets

CAPACITIVE HUMIDITY SENSOR

CROSS REFERENCE TO RELATED APPLICATION

This application is based on Japanese Patent Application No. 2004-267206 filed on Sep. 14, 2004, the disclosure of which is incorporated herein by reference.

FIELD OF THE INVENTION

The present invention relates to a capacitive humidity sensor having a humidity sensitive layer.

BACKGROUND OF THE INVENTION

A capacitive humidity sensor, disclosed in JP-U-5-23124, has a humidity sensitive layer interposed between a pair of electrodes. Relative permittivity of the humidity sensitive layer is changed in response to humidity.

In this sensor, the electrodes are arranged opposite to each other on a surface of an insulating substrate, and the humidity sensitive layer (a dielectric material) is disposed on the electrodes. Further, a circuit section such as a signal processing circuit for a capacitance change between the electrodes is disposed in a substrate separated from the insulating substrate. Therefore, the electrodes are required to be electrically connected to the circuit section using bonding wires or lead wires or the like. Therefore, it is difficult to reduce the whole size of the sensor including the circuit section.

In a capacitive humidity sensor disclosed in U.S. Pat. No. 6,580,600 (corresponding to JP-A-2002-243690), a pair of electrodes and a humidity sensitive layer are integrated with a circuit section on a semiconductor substrate. The electrodes are electrically connected to the circuit section through wiring formed on the semiconductor substrate. Therefore, the whole size of the sensor can be reduced.

In the sensor using a semiconductor substrate, however, semiconductor process technology is essential to form the electrodes, the humidity sensitive layer and the circuit section. Therefore, complex process and expensive equipment are required to manufacture the sensor in addition to high cost of a semiconductor substrate. Accordingly, the manufacturing cost of the sensor increases.

SUMMARY OF THE INVENTION

In view of the above-described problem, it is an object of the present invention to provide a capacitive humidity sensor including a sensor section, which has a reduced size while being manufactured in low cost.

A capacitive humidity sensor of an embodiment of the present invention includes a printed circuit board having an insulating substrate on which a circuit section is disposed, a pair of electrodes disposed on a surface of the insulating substrate, opposite from each other with a space, a humidity sensitive layer disposed on the insulating substrate to cover the electrodes and the surface of the insulating substrate between the electrodes, and a wiring section provided in the insulating substrate. In this sensor, the humidity sensitive layer has a relative permittivity which changes in response to a humidity, the electrodes and the circuit section are electrically connected through the wiring section, and the circuit section performs a signal processing of a capacitance change between the electrodes. Accordingly, the electrodes, the circuit section and the wiring section can be integrated with the insulating substrate, and the whole size of the sensor including the circuit section can be reduced.

Further, the electrodes, the humidity sensitive layer and the circuit section can be formed on the insulating substrate using a common manufacturing technique (e.g., patterning of conductive foil or screening printing) for a printed circuit board. Therefore, the electrodes and the humidity sensitive layer can be easily integrated with the circuit section, and the sensor can be manufactured at low cost.

For example, the circuit section is disposed on one surface of the insulating substrate, and the electrodes and the humidity sensitive layer are disposed on a back surface of the insulating substrate, opposite to the one surface. In this case, a protective layer having a moisture proof property can be disposed to cover the circuit section.

Furthermore, the wiring section can be disposed inside the insulating substrate to penetrate through the insulating substrate. As an example, the insulating substrate has a via hole, and the wiring section has a connection material filled in the via hole. Alternatively, the insulating substrate has a through hole, and the wiring section has an electrical conductor arranged on a wall surface for defining the through hole. Accordingly, the wiring section is hardly affected by external force. In addition, reliability of electrical connection between the electrodes and the circuit section can be improved, as compared with a case where the electrodes and the circuit section are connected through bonding wires.

The circuit section and the electrodes can be arranged on the same surface of the insulating substrate. In this case, the wiring section includes a conductive pattern arranged inside the insulating substrate, a first connection portion through which the circuit section is electrically connected to the conductive pattern, and a second connection portion through which the electrodes are electrically connected to the conductive pattern. For example, the first and second connection portions extend from the conductive pattern inside the insulating substrate to the surface where the circuit section and the electrodes are located.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENTS

First Embodiment

Figure 1A:
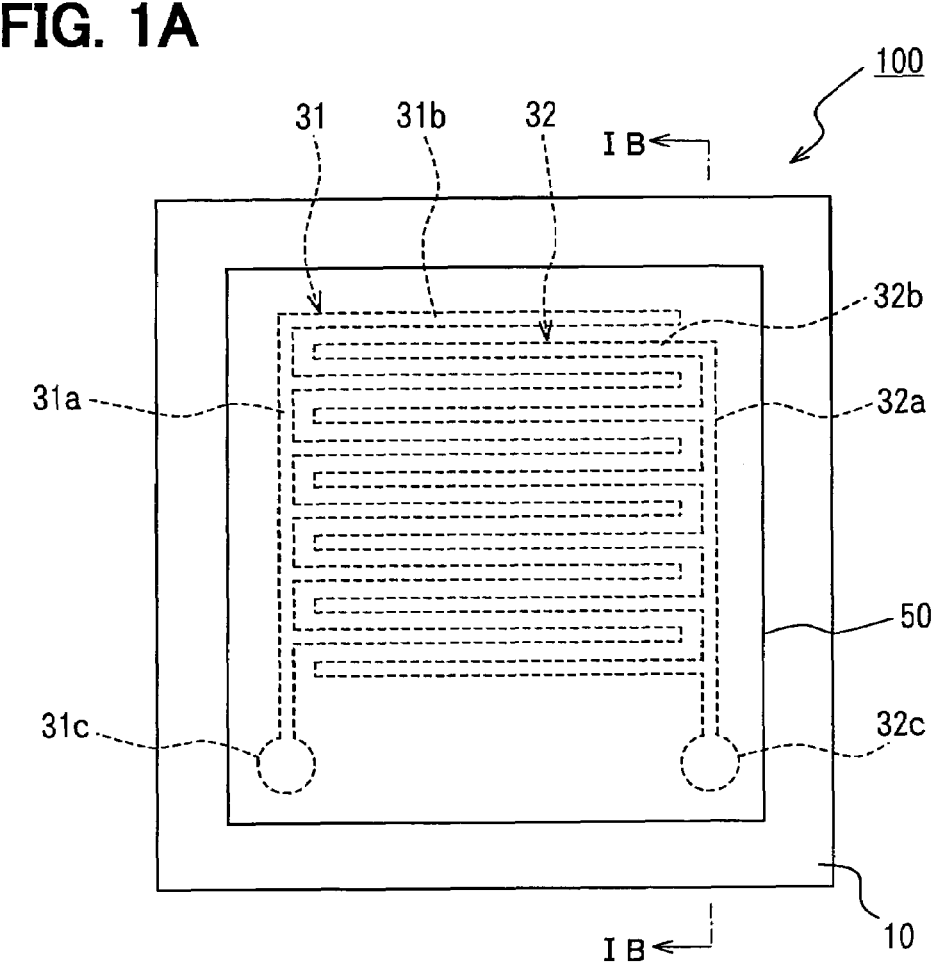
FIG. 1A is a schematic view showing a capacitive humidity sensor according to a first embodiment of the present invention.
Figure 1B:
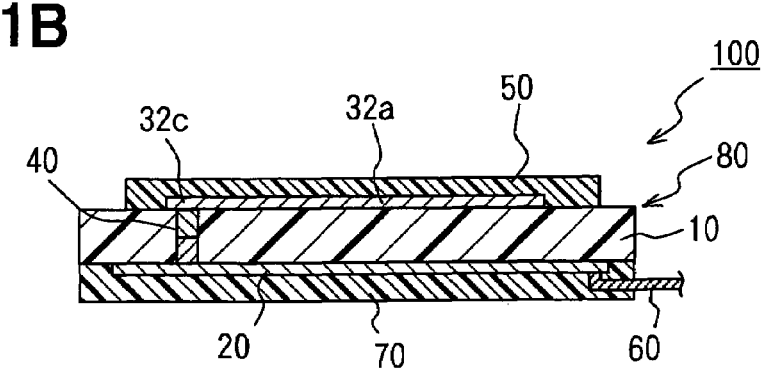
FIG. 1B is a cross-sectional view showing the sensor taken along line IB-IB in FIG. 1A.

A capacitive humidity sensor 100 according to the first embodiment of the present invention is shown in FIGS. 1A and 1B. In this embodiment, an electrical insulating material commonly used for a printed circuit board (PCB) is typically used as an insulating substrate 10. As an example, in the sensor 100, the insulating substrate 10 is formed from multiple layers (e.g., two layers in this embodiment) of thermoplastic resin films, which are made of liquid crystal polymer (LCP) and laminated together under pressure and heat.

A circuit section 20 is formed on one surface of the insulating substrate 10 as a part of a circuit pattern of a printed circuit board 80. The circuit section 20 performs a signal processing of a capacitance change between a pair of electrodes 31, 32. The circuit section 20 is composed of the part of the circuit pattern and electronic components (not shown) mounted thereon. In order to form the circuit section 20, conductive foil is bonded to a surface of one of thermoplastic resin films and is formed into a predetermined pattern by etching. Gold (Au), silver (Ag), copper (Cu), aluminum (Al) or the like can be used as a material of the conductive foil. As an example, copper (Cu) foil can be used in the sensor 100. Furthermore, the circuit section 20 can be formed by screen-printing.

The electrodes 31, 32 are formed on the back surface of the insulating substrate 10, to be opposite from each other with a gap. The electrodes 31, 32 include common electrodes 31a, 32a and comb-teeth electrodes 31b, 32b extending from the common electrodes 31a, 32a in one direction, respectively. The comb-teeth electrodes 31b are arranged alternately with the comb-teeth electrodes 32b. When the electrodes 31, 32 are comb-shaped, the comb-teeth electrodes 31b, 32b can be made opposite to each other along a long distance, and thereby capacitance between the electrodes 31, 32 can be made larger within a small space. In this embodiment, a change rate of capacitance between the electrodes 31, 32, which changes in response to a change in ambient humidity, increases accordingly. As a result, humidity sensitivity of the sensor 100 can be improved.

The electrodes 31, 32 are formed as a part of a circuit pattern of the printed circuit board 80 and can be formed by the same process as the circuit section 20. Specifically, conductive foil made of copper (Cu) adheres on one surface of the other thermoplastic resin film and is formed into a predetermined shape by etching. Alternatively, the electrodes 31, 32 can be formed by screen printing.

As shown in FIG. 1A, the electrodes 31, 32 have lands 31c, 32c at ends of the common electrodes 31a, 32a, respectively. The lands 31c, 32c are connected to wiring sections 40 through which the electrodes 31, 32 and the circuit section 20 are electrically connected.

The wiring sections 40 are formed in the insulating substrate 10 as a part of a circuit pattern of the printed circuit board 80. Here, a method of forming the wiring sections 40 will be now described. Via holes are formed in each of the thermoplastic resin films for forming the insulating substrate 10. The via holes of one of the thermoplastic resin films are exposed to the circuit section 20. Likewise, the via boles of the other thermoplastic resin film are exposed to the electrodes 31, 32 (land 31c, 32c). A connection material (e.g., a conductive paste of Silver (Ag) and Tin (Sn)) for forming the wiring sections 40 is filled in each via hole. Then, the thermoplastic resin films are stacked, and heating and pressing are performed so that the connection materials in the via holes of the thermoplastic resin films are joined to each other. Further, the connection materials in. the via holes of the thermoplastic resin films are joined to the circuit section 20 and the electrodes 31, 32. Therefore, the circuit section 20 and the electrodes 31, 32 are electrically connected though the wiring sections 40 made of the connection material. The conductive material can be filled in the via holes using a screen printer or a dispenser or the like (not shown).

A humidity sensitive layer 50 is formed on the substrate 10 to cover the electrodes 31, 32 and the substrate 10 between the electrodes 31, 32. The humidity sensitive layer 50 can be made of a polymeric material having hygroscopic property, such as polyimide polymer and cellulose acetate butyrate polymer. As an example, the humidity sensitive layer 50 is made of polyimide polymer in this embodiment. There are some methods to form the humidity sensitive layer 50. In this embodiment, the humidity sensitive layer 50 is formed by screen printing because a photo process essential to pattering can be omitted.

In the sensor 100, when water (moisture) in the air infiltrates into the humidity sensitive layer 50, the relative permittivity of the humidity sensitive layer 50 changes in accordance with the amount of infiltrated water due to a large relative permittivity of water. Then, capacitance between the electrodes 31, 32 changes in response to the change of the relative permittivity of the humidity sensitive layer 50, because a capacitor is constructed with the electrodes 31, 32 using the humidity sensitive layer 50 as a part of a dielectric material. The amount of water infiltrated into the humidity sensitive layer 50 depends on humidity around the sensor 100. Therefore, the capacitance between the electrodes 31, 32 changes according to the humidity. Then, the circuit section 20 performs a signal processing (e.g., Capacitance to Voltage conversion) of the capacitance change between the electrodes 31, 32, and thereby, the sensor 100 can detect humidity.

A pad is formed at one end of the circuit section 20 and a connector 60 is connected to the pad through a junction material such as solder. The connector 60 is used as an external connection terminal. A protective layer 70 is disposed on the substrate 10 to cover the circuit section 20 in a state where the connector 60 is connected to the pad of the circuit section 20. An insulating material having moisture-proof property can be used as a material for forming the protective layer 70. For example, gel (e.g., fluoride gel or silicone gel), HumiSeal (e.g., acrylic 1B66), or resin (e.g., epoxy resin) can be used as the material for forming the protective layer 70.

In the sensor 100, the protective layer 70 can be made of liquid crystal polymer (LCP), which is thermoplastic resin. When the protective layer 70 is made of thermoplastic resin, the protective layer 70 can be used not only as a protective layer, but also as a contact surface through which the sensor 100 is installed to another body. Packaging can be omitted when the protective layer 70 is used.

The protective layer 70 is fixed to the insulating substrate 10 as follows. First, the protective layer 70 is disposed on the substrate 10 to cover the circuit section 20 to which the connector 60 is attached. After that, pressure and heat are applied to the protective layer 70 by using a heating tool or the like. In this case, the protective layer 70 is softened and the circuit section 20 including the connector 60 is buried therein. Thus, the circuit section 20 can be covered with the protective layer 70. Further, because the insulating substrate 10 is made of liquid crystal polymer (LCP), the insulating substrate 10 and the protective layer 70 are bonded (welded) together, and the protective layer 70 can be fixed to the insulating substrate 10.

As described above, the printed circuit board 80 includes the insulating substrate 10, the circuit section 20, the electrodes 31, 32 and the wiring sections 40. In short, the circuit section 20, the electrodes 31, 32 and the wiring sections 40 are formed as a circuit pattern in the printed circuit board 80. The electrodes 31, 32 and the circuit section 20 are connected through the wiring sections 40 formed on the insulating substrate 10. Therefore, the whole size of the sensor 100 including the circuit section 20 can be reduced.

In the sensor 100, the circuit section 20 is formed on one surface of the insulating substrate 10, and the electrodes 31, 32 including the humidity sensitive layer 50 are formed on the other surface of the insulating substrate 10. That is, the circuit section 20 and the electrodes 31, 32 including the humidity sensitive layer 50 are not on the same surface of the insulating substrate 10. Therefore, the surface area of the sensor 100 can be effectively reduced. Further, the facing area of the electrodes 31, 32 can be increased without increasing the size of the sensor 100, and accordingly humidity sensitivity of the sensor 100 can be improved.

The surface of the circuit section 20 is covered with the protective layer 70 having a moisture-proof property. Therefore, the circuit section 20 can be prevented from being corroded, even when the circuit section 20 is integrated with the insulating substrate 10.

Further, a material such as gel, which is difficult to be applied to a small area, can be used for forming the protective layer 70. In this embodiment, the circuit section 20 is formed on the back surface of the insulating substrate 10, opposite to a surface where the electrodes 31, 32 are formed. Therefore, even when gel is used for forming the protective layer 70, the protective layer 70 can be easily formed on the circuit section 20 without spreading on the electrodes 31, 32 and the humidity sensitive layer 70. Thus, delay in response of the sensor 100, which is caused by the protective layer 70 spreading on the electrodes 31, 32 and the humidity sensitive layer 50, can be prevented, even if the gel is used for forming the protective layer 70.

As described above, the sensor 100 can be manufactured by common manufacturing technique for a printed circuit board (e.g., pattering of conductive foil and screening printing). Therefore, the electrodes 31, 32 and the humidity sensitive layer 50 can be easily integrated with the circuit section 20, and the sensor 100 can be manufactured at low cost. The electrodes 31, 32 and the circuit section 20 are formed as a part of a circuit pattern of the printed circuit board 80. Therefore, the sensor 100 has a high flexibility in pattern design, and pattern layout can be easily changed, as compared with a sensor using a semiconductor substrate.

In the sensor 100, the wiring sections 40 for electrically connecting the electrodes 31, 32 and the circuit section 20 are located in the insulating substrate 10. Therefore, the wiring sections 40 are hardly affected by external forces (e.g., shrinkage and expansion caused by temperature change of the protective layer 70 on the circuit section 20). In addition, reliability of electrical connection between the electrodes 31, 32 and the circuit section 20 can be improved, as compared with a case where the electrodes 31, 32 and the circuit section 20 are connected through bonding wires or the like. Further, the wiring sections 40 can be prevented from being corroded without using an additional layer for moisture proofing, because the wiring sections 40 are sealed with the insulating substrate 10, the electrodes 31, 32 (land 31c, 32c) and the circuit section 20.

In the above-described first embodiment, the wiring section 40 for connecting the electrode 31 and the circuit section 20 and the wiring section 40 for connecting the electrode 32 and the circuit section 20 can be constructed with a single member.

Second Embodiment

A capacitive humidity sensor 200 of the second embodiment will be now described with reference to FIG. 2.

In the sensor 100 of the above-described first embodiment, the electrodes 31, 32 and the circuit section 20 are formed on different surfaces of the insulating substrate 10. In contrast, in the capacitive humidity sensor 200 of the second embodiment, electrodes 31, 32 and a circuit section 20 are formed on the same surface of an insulating substrate 10.

In the sensor 200, the electrodes 31, 32 and the circuit section 20 are electrically connected through wiring sections 40 formed in the insulating substrate 10. The electrodes 31, 32, a humidity sensitive layer 50, the circuit section 20 and the wiring sections 40 are integrated to the insulating substrate 10. Therefore, the whole size of the sensor 200 including the circuit section 20 can be effectively reduced.

Figure 2:
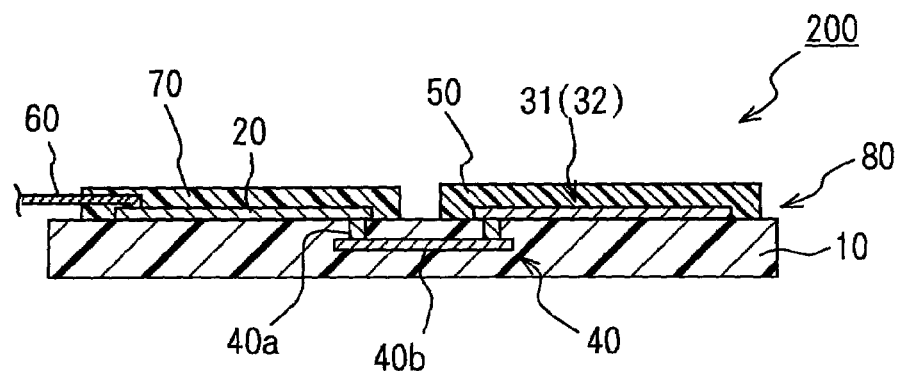
FIG. 2 is a cross-sectional view showing a capacitive humidity sensor according to a second embodiment of the present invention.

As shown in FIG. 2, a connection material is filled in via holes to form connection portions 40a, and a conductor pattern 40b is disposed inside the insulating substrate 10. The wiring sections 40 are composed of the conductor pattern 40b, and the connection portions 40a connected to the conductor pattern 40b.

The circuit section 20, the electrodes 31, 32 and the wiring sections 40 are formed as a circuit pattern of a printed circuit board 80. Therefore, the whole size of the sensor 200 including the circuit section 20 can be reduced, compared with a sensor having the circuit section 20 as an external circuit, which are electrically connected to the electrodes 31, 32 through bonding wires or lead wires.

In the sensor 200 of this embodiment, the electrodes 31, 32 and the circuit section 20 are formed on the same surface of the insulating substrate 10. Therefore, the electrodes 31, 32 and the circuit section 20 can be made of the same material, and can be formed in the same process. For example, copper (Cu) foil is used as a material for forming the electrodes 31, 32 and the circuit section 20, and thereby simplifying the manufacturing process and reducing the manufacturing cost.

The sensor 200 can be manufactured by common manufacturing techniques for a printed circuit board (e.g., pattering of conductive foil and screening printing). In this case, the manufacturing cost of the sensor 200 can be reduced. Besides, the electrodes 31, 32 and the circuit section 20 are formed as a part of a circuit pattern of the printed circuit board 80. Therefore, the sensor 200 has a high flexibility in pattern design, and pattern layout can be easily changed, as compared with the sensor using a semiconductor substrate.

In the sensor 200, reliability of electrical connection between the electrodes 31, 32 and the circuit section 20 can be improved, because the electrodes 31, 32 and the circuit section 20 are electrically connected through the wiring sections 40 integrated in the insulating substrate 10. The wiring sections 40 can be prevented from being corroded without an additional layer for moisture proofing, because it is sealed with the insulating substrate 10, the electrodes 31, 32 (land 31c, 32c) and the circuit section 20.

In the sensor 200, the electrodes 31, 32 and the circuit section 20 are formed on the same surface of the insulating substrate 10. Therefore, a material that can be applied to a small area is suitable for forming the protective layer 70 in order to prevent delay in response of the sensor 200. For example, HumiSeal or thermoplastic resin can be used for forming the protective layer 70. HumiSeal coatings can be performed by brushing or dipping (by dipping a predetermined part into HumiSeal solution). Then, the HumiSeal coated part is left out at room temperature for about 30 minutes, and consequently the protective layer 70 having moisture proof properties is formed. Thermoplastic resin can be used for forming the protective layer 70, similarity to the above-described first embodiment.

OTHER EMBODIMENTS

Althrough the present invention has been described in connection with some preferred embodiments thereof with reference to the accompanying drawings, it is to be noted that various changes and modifications will become apparent to those skilled in the art.

For example, in the above-described first embodiment, the via holes are formed and a conductor material is filled in the via holes, so that the wiring section 40 is formed. However, in a capacitive humidity sensor 300 shown in FIGS. 3A and 3B, through holes 11 are formed in an insulating layer 10, and wiring sections 40 are coated on wall portions of the through holes 11, so that electrodes 31, 32 and a circuit section 20 are electrically connected through the wiring sections 40.

Figure 3A:
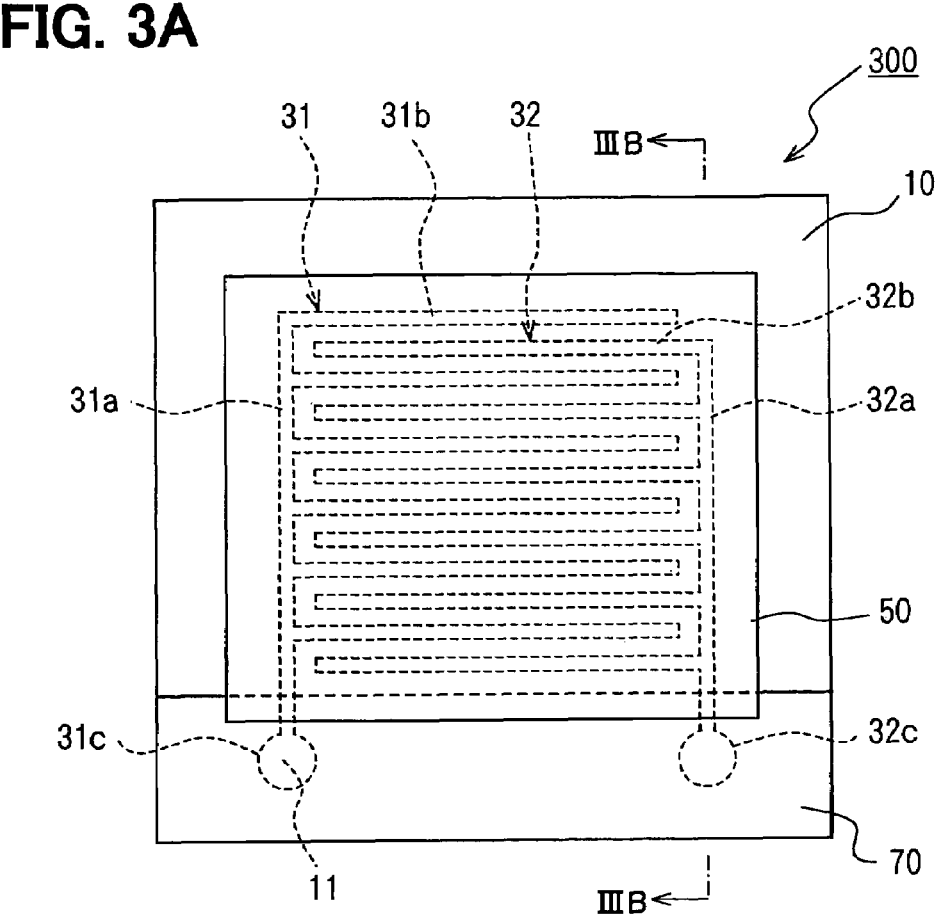
FIG. 3A is a schematic view showing a capacitive humidity sensor according to a modification of the present invention.
Figure 3B:
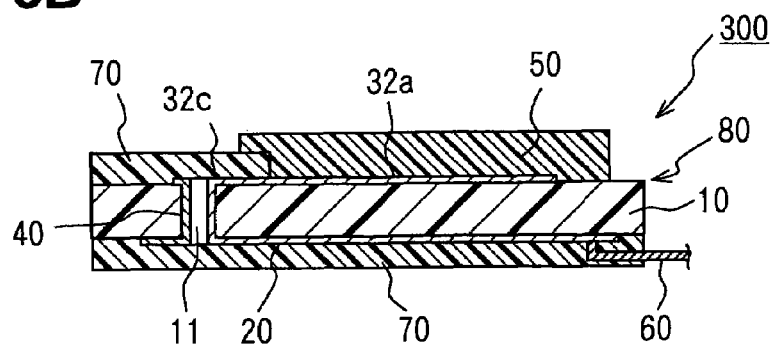
FIG. 3B is a cross-sectional view showing the sensor taken along line IIIB-IIIB in FIG. 3A.

In the sensor 300 shown in FIGS. 3A and 3B, a humidity sensitive layer 50 is disposed to cover not the whole area of electrodes 31, 32, but a part of the electrodes 31, 32 (the comb-teeth electrodes 31b, 32b and a part of the common electrodes 31a, 32a) that have an effect on capacitance change. A protective layer 70 is disposed on the uncovered part of electrodes 31, 32 that is susceptible to corrosion due to exposure to air. In this case, a humidity sensitive layer 50 is disposed on the insulating substrate 10 after the protective layer 70 is formed on the insulating substrate 10. HumiSeal or thermoplastic resin are suitable for forming the protective layer 70, because the protective layer 70 is required to be disposed on the electrodes 31, 32 uncovered by the humidity sensitive layer 50.

In the above-described sensor 100 of the first embodiment, the electrodes 31, 32 are entirely covered with the humidity sensitive layer 50. However, the electrodes 31, 32 may be corroded due to infiltrated water into the humidity sensitive layer 50. If there is a possibility that the corrosion of the electrodes 31, 32 will be caused, a protective film (e.g., silicon nitride film) can be disposed to cover the electrodes 31, 32 and the insulating substrate 10 between the electrodes 31, 32. Thereafter, the humidity sensitive layer 50 can be disposed on the insulating substrate 10 through the protective film.

When the electrodes 31, 32 are made of noble metal (e.g., gold (Au)), the corrosion preventing effect can be effectively improved. Likewise, the circuit section 20 can be made of noble metal (e.g., gold (Au)) for improving the corrosion preventing property. In this case, the protective layer 70 may be omitted.

In the above-described sensor 100, the insulating substrate 10 of the printed circuited board 80 is formed from two layers of thermoplastic resin films. However, the number of the layers and the material for forming the layers can be suitably changed. For example, the insulating substrate 10 of the printed circuited board 80 can be formed by a single layer of the thermoplastic resin film.

Likewise, the structure of the wiring sections 40 can be suitably changed, as long as the wiring sections 40 are formed on/in the insulating substrate 10 as a part of a circuit pattern of the printed circuit board 80 and electrically connects the electrodes 31, 32 and the circuit section 20. For example, the wiring sections 40 can be disposed on the surface of the insulating substrate 10 as a conductor pattern not inside the insulating substrate 10.

In the above-described sensor 100, the connector 60 is used as an external connection terminal. However, the external connection terminal is not limited to the connector 60.

While the invention has been described with reference to preferred embodiments thereof, it is to be understood that the invention is not limited to the preferred embodiments and constructions. The invention is intended to cover various modification and equivalent arrangements. In addition, while the various elements of the preferred embodiments are shown in various combinations and configurations, which are preferred, other combinations and configuration, including more, less or only a single element, are also within the spirit and scope of the invention.

What is claimed is:

1. A capacitive humidity sensor comprising:
   a printed circuit board having an insulating substrate on which a circuit section is disposed;
   a pair of electrodes disposed on a surface of the insulating substrate, opposite from each other with a space;
   a humidity sensitive layer disposed on the insulating substrate to cover the electrodes and the surface of the insulating substrate between the electrodes, the humidity sensitive layer having a relative permittivity which changes in response to a humidity; and
   a wiring section provided in the insulating substrate, through which the electrodes and the circuit section are electrically connected, wherein
   the circuit section is configured to perform a signal processing of a capacitance change between the electrodes,
   wherein the circuit section is disposed on one surface of the insulating substrate, and
   wherein the electrodes and the humidity sensitive layer are disposed on a back surface of the insulating substrate, opposite to the one surface.

2. The sensor according to claim 1, further comprising:
   a protective layer having a moisture proof property, which covers the circuit section.

3. The sensor according to claim 2, further comprising:
   a terminal connector connectable to an exterior circuit, wherein
   the protective layer is made of thermoplastic resin, and
   the protective layer covers the circuit section in a state where the terminal connector is connected to the circuit section.

4. The sensor according to claim 1, wherein the wiring section is disposed inside the insulating substrate to penetrate through the insulating substrate.

5. The sensor according to claim 4, wherein
   the insulating substrate has a via hole, and
   the wiring section has a connection material filled in the via hole.

6. The sensor according to claim 4, wherein
   the insulating substrate has a through hole, and
   the wiring section has an electrical conductor arranged on a wall surface for defining the through hole.

7. The sensor according to claim 1, wherein
   each of the electrodes includes a common electrode portion and a plurality of comb-teeth electrode portions extending from the common electrode portion in one direction, and
   the comb-teeth electrode portions of one of the electrodes and the comb-teeth electrode portions of the other one of the electrodes are alternately arranged with a space.

* * * * *